US009128046B2

(12) United States Patent
Samson et al.

(10) Patent No.: US 9,128,046 B2
(45) Date of Patent: Sep. 8, 2015

(54) SLIDE HOLDER ASSEMBLY FOR COMET ASSAY

(71) Applicant: Cellomics, Inc., Pittsburgh, PA (US)

(72) Inventors: Brent A. Samson, Eighty Four, PA (US); Chandrasekaran Vasudevan, Baden, PA (US); Keith R. Heffley, Pittsburgh, PA (US); Joseph M. Zock, Rio Rancho, NM (US); Dirk John Vandenberg, III, Wilkinsburgh, PA (US)

(73) Assignee: CELLOMICS, INC., Pittsburgh, PA (US)

( * ) Notice: Subject to any disclaimer, the term of this patent is extended or adjusted under 35 U.S.C. 154(b) by 108 days.

(21) Appl. No.: 13/658,263

(22) Filed: Oct. 23, 2012

(65) Prior Publication Data

US 2013/0105320 A1     May 2, 2013

Related U.S. Application Data

(60) Provisional application No. 61/553,409, filed on Oct. 31, 2011.

(51) Int. Cl.
*G01N 27/447*    (2006.01)
*B01L 3/00*    (2006.01)
(Continued)

(52) U.S. Cl.
CPC ............ *G01N 27/44756* (2013.01); *B01L 3/50* (2013.01); *B01L 3/5085* (2013.01); *B01L 3/50853* (2013.01); *B01L 9/00* (2013.01); *G01N 27/453* (2013.01)

(58) Field of Classification Search
CPC ......... B01L 9/00; B01L 3/50; B01L 3/50853; G01N 27/447; G01N 27/453

USPC .................................. 204/461, 456; 422/563
See application file for complete search history.

(56) References Cited

U.S. PATENT DOCUMENTS 5,445,723 A * 8/1995 Camacho ...................... 204/614
6,118,582 A * 9/2000 Del Buono .................... 359/398
(Continued)

FOREIGN PATENT DOCUMENTS

CN      201222052         4/2009
GB      2466816 A *       7/2010
(Continued)

OTHER PUBLICATIONS

Product Manual, OxiSelect™ Comet Assay Kit (3-Well Slides), Cell Biolabs, Inc., 9 pages, 2008.
(Continued)

*Primary Examiner* — Jennifer Dieterle
(74) *Attorney, Agent, or Firm* — Workman Nydegger

(57) ABSTRACT

A slide holder assembly and method for use in high content screening of a comet assay. The slide holder assembly has an inside surface and is configured to receive a slide holding a plurality of biological cells on a top surface thereof. When the slide is secured within the slide holder assembly, the inside surface of the slide holder assembly and the top surface of the slide combine to form a cavity having an open top end. The cavity is watertight and configured to hold a liquid therein. A method of performing a comet assay using a slide disposed within a slide holder assembly. The method includes performing encapsulation, lysis, electrophoresis, staining, and imaging of cells on the slide while the slide remains secured within the slide holder assembly.

24 Claims, 12 Drawing Sheets

(51) Int. Cl.
  *B01L 9/00*   (2006.01)
  *G01N 27/453*   (2006.01)

(56) References Cited

U.S. PATENT DOCUMENTS

| | | | |
|---|---|---|---|
| 6,379,516 | B1 | 4/2002 | Cabilly et al. |
| 7,452,712 | B2 * | 11/2008 | Fawcett .................... 435/288.4 |
| 7,666,362 | B2 * | 2/2010 | Shanler ...................... 422/401 |
| 7,833,708 | B2 | 11/2010 | Enzelberger et al. |
| 2003/0129756 | A1 * | 7/2003 | Thorne et al. .................. 436/46 |
| 2004/0115709 | A1 * | 6/2004 | Morozov et al. ................ 435/6 |
| 2005/0135974 | A1 * | 6/2005 | Harvey et al. ................ 422/102 |
| 2012/0058467 | A1 * | 3/2012 | Thomas et al. ............... 435/6.1 |

FOREIGN PATENT DOCUMENTS

| | | |
|---|---|---|
| WO | 02/077630 A1 | 10/2002 |
| WO | 2004/074818 A2 | 9/2004 |
| WO | 2006/119941 A1 | 11/2006 |
| WO | 2009/134768 A1 | 11/2009 |

OTHER PUBLICATIONS

Product Manual, *Standardized CometAssay™ System*, Trevigen, Inc., 16 pages, 2009.

ThorLabs V21 Catalog, p. 209, published at least as early as Oct. 2011.

European extended search report dated Mar. 6, 2013 issued in related European Application No. 12189777.1, filed Oct. 24, 2012.

* cited by examiner

SLIDE HOLDER ASSEMBLY FOR COMET ASSAY

CROSS REFERENCE TO RELATED APPLICATIONS

This application claims priority to U.S. Provisional Patent Application No. 61/553,409, filed on Oct. 31, 2011, the contents of which are hereby incorporated by reference.

BACKGROUND OF THE INVENTION

1. The Field of the Invention

The present invention relates to assay methods to predict compound toxicity.

2. The Relevant Technology

The comet assay, also known as Single Cell Gel Electrophoresis (SCGE), is a standard assay commonly used to measure the induction of DNA damage by acute exposure to chemicals or radiation. The comet assay was first described by Singh et al. in 1988. It has since gained in popularity as a standard technique for evaluation of DNA damage/repair, biomonitoring and genotoxicity testing. A comet assay involves the encapsulation of cells in a low-melting-point agarose (LMA) suspension, lysis of the cells in neutral or alkaline conditions to break down the cell membranes and leave the nuclear area (or nucleoid), and electrophoresis of the layered nucleoids. This is followed by visual analysis with staining of DNA and calculating fluorescence to determine the extent of DNA damage.

The concept underlying the comet assay is that undamaged DNA retains a highly organized association with matrix proteins in the nucleus. When damaged, this organization is disrupted. The individual strands of DNA lose their compact structure and relax, expanding out of the cavity into the agarose. When an electric field is applied across the DNA, which has an overall negative charge, the DNA is drawn towards the anode, which is positively charged. Undamaged DNA strands are too large and do not leave the cavity, whereas damaged fragments do. The smaller the fragments, the farther they are free to move in a given period of time. Therefore, the amount of DNA that leaves the cavity is a measure of the amount of DNA damage in the cell.

The image analysis measures the overall intensity of the fluorescence for the whole nucleoid and the fluorescence of the migrated DNA and compares the two signals. The stronger the signal from the migrated DNA, the more damage there is present. The overall structure resembles a comet (hence "comet" assay) with a circular head corresponding to the undamaged DNA that remains in the cavity and a tail of damaged DNA. The brighter and longer the tail, the higher the level of damage.

The comet assay is a versatile technique for detecting damage and with adjustments to the protocol can be used to quantify the presence of a wide variety of DNA altering lesions (damage). The damage usually detected is single strand breaks and double strand breaks. Additional DNA structures can be detected as DNA damage, such as AP sites (abasic sites missing either a pyrimidine or purine nucleotide) and sites where excision repair is taking place.

Conventionally, the cells are encapsulated on a slide that contains one or more wells. Lysis occurs by placing the slide into a container and exposing the slide to a lysing reagent. Containers used in conventional comet assays may require up to a liter of lysing reagent to cover the slide. The slide is then transferred to an electrophoresis chamber, where the slide is exposed to an electrophoresis buffer solution and an electric current is passed over the slide. Conventional electrophoresis chambers may require up to a liter of electrophoresis buffer solution to cover the slide. The slide is then removed from the electrophoresis chamber, stained with a fluorescent dye, and imaged through a microscope to determine the extent of DNA damage. This is performed by manual scoring by eye or automatically by imaging software.

While conventional assaying systems provide acceptable results when used in performing comet assays, the systems have some significant problems. For example, as noted above, up to a liter of lysing reagent and a liter of electrophoresis buffer are often required to carry out a comet assay on a single slide. After use, these solutions must be discarded. However, the solutions are not environmentally friendly, and special care must be taken in their disposal. It would be a great benefit to provide an assaying system that minimized the use of these solutions. Another problem with the present approach is that slides must be moved between different containers to perform the steps of the comet assay. The cells that are encapsulated on the slide can be very delicate and affected by the movement. Therefore, it would be a benefit to minimize the movement of the slide between different containers. Furthermore, by requiring movement between different containers, the conventional assaying system does not lend itself well to automated or robotic handling of the slides during the comet assay.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION OF THE PREFERRED EMBODIMENTS

As used in the specification and appended claims, directional terms, such as "top," "bottom," "up," "down," "upper," "lower," "proximal," "distal," and the like are used herein solely to indicate relative directions and are not otherwise intended to limit the scope of the invention or claims.

The present invention relates to various apparatuses and methods for performing a cellular assay that allow the slide or slides that hold the cells to remain in a common slide holder assembly during all phases of the assay, including imaging. In particular, the present invention relates to performing comet assays using the slide holder assembly.

Although the discussion herein is directed to comet assays, other types of assays may also be performed using embodiments of the present invention. For example, fluorescent in-situ hybridization (FISH) protocols which use DNA sequence specific probes such as those for detecting BCR-ABL (Philadelphia chromosome) can be processed using embodiments of the present invention with or without comet analysis. In yet another example, various immunohistochemical staining protocols can be performed on non-comet samples such as cells or tissue slides using embodiments of the present invention. Other types of assays may also be performed.

In one embodiment, the slide holder assembly is not inserted into the imaging system until after various phases of the assay have been completed and the slide(s) within the slide holder assembly is(are) ready for imaging.

In another embodiment, the slide holder assembly and associated slide(s) can also be positioned within the imaging system during one or more of the non-imaging phases of the assay. In this embodiment, an automated system can be used to perform the non-imaging phases of the assay, along with imaging, analysis, and data visualization.

Figure 1:
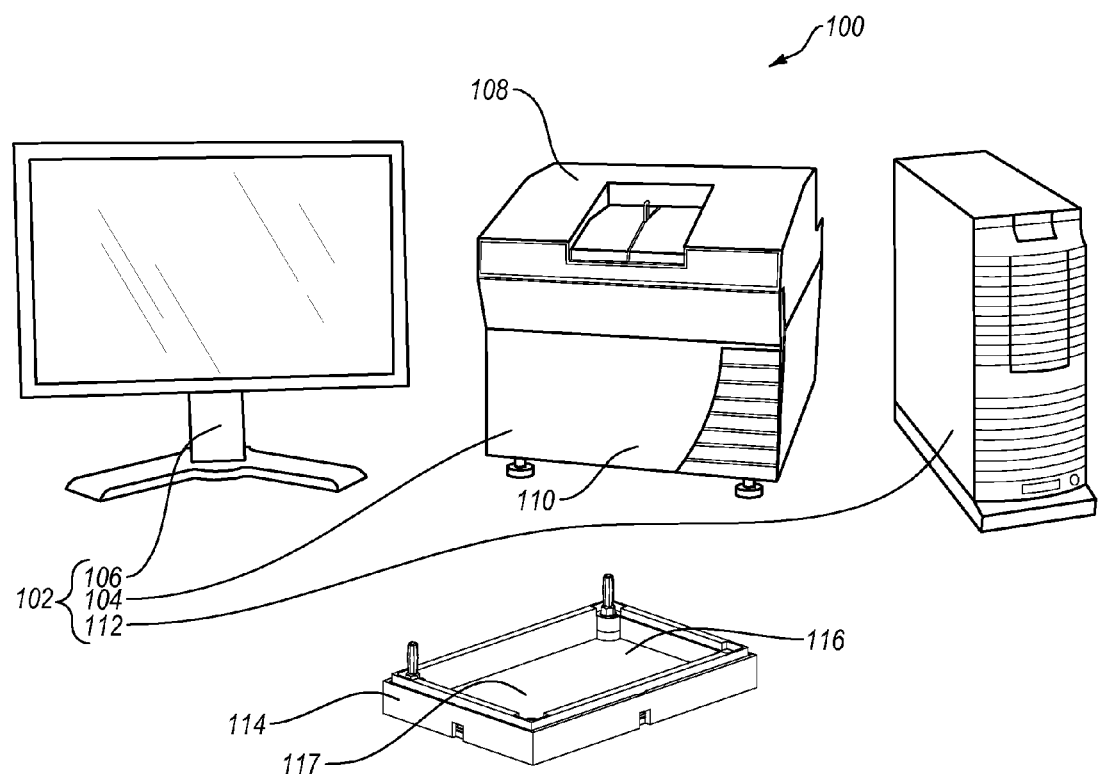
FIG. 1 is a front perspective view of an exemplary system incorporating features of the present invention.

FIG. 1 is a block diagram illustrating an exemplary assay system 100 incorporating features of the present invention. At the heart of the assay system is a quantitative high-content cell imaging system 102 in which cells are scanned and analyzed. The exemplary cell imaging system 102 includes, but is not limited to, an imaging device 104 with a user display device 106. Imaging device 104 generally includes a stage housing 108 mounted on a microscope assembly 110 having a plurality of objectives. Stage housing 108 is configured to house the components required to position a specimen plate or slide containing cells so microscope assembly 110 can image the cells using the objectives to allow high content screening of the cells to be performed, as is known by one skilled in the art. Analyzing and storing of the data obtained from the imaging can be performed by imaging device 104 with results being displayed to the user on user display device 106. Examples of commercially available high content cell imaging systems that can be used are the Thermo Scientific® ToxInsight® IVT Platform manufactured by Cellomics, Inc. of Pittsburgh, Pa., a subsidiary of Thermo Fisher Scientific, Inc. and the Thermo Scientific® ArrayScan® VTI HCS Reader, also manufactured by Cellomics, Inc. Other cell imaging systems can also be used.

Cell imaging system 102 can also include an external computing device 112, if desired. External computing device 112 can comprise a general purpose or specialized computer or server or the like. External computing device 112 can be used as a controller for the system as well as for performing, by itself or in conjunction with imaging device 104, the analyzing and/or storing of the data obtained by imaging device 104. In some embodiments, external computing device 112 can also display results to the user on user display device 106. External computing device 112 can communicate with imaging device 104 and/or display device 106 directly or through a network, as is known in the art.

An operating environment for one or more of the devices of cell imaging system 102 can include a processing system with one or more high speed Central Processing Unit(s) ("CPU"), processors and one or more memories, as are known in the art.

Assay system 100 is configured to allow a comet assay to be performed therewith. As such, assay system 100 can also include one or more slide holder assemblies 114 used to house a slide 116 as the comet assay is performed on cells encapsulated on a top surface 117 of the slide. Slide holder assembly 114 is configured to allow all of the steps of the comet assay, including high content imaging, to be performed on slide 116 as the slide is retained within slide holder assembly 114. In some embodiments, all or a portion of the slide holder assembly can be reusable.

Figure 2:
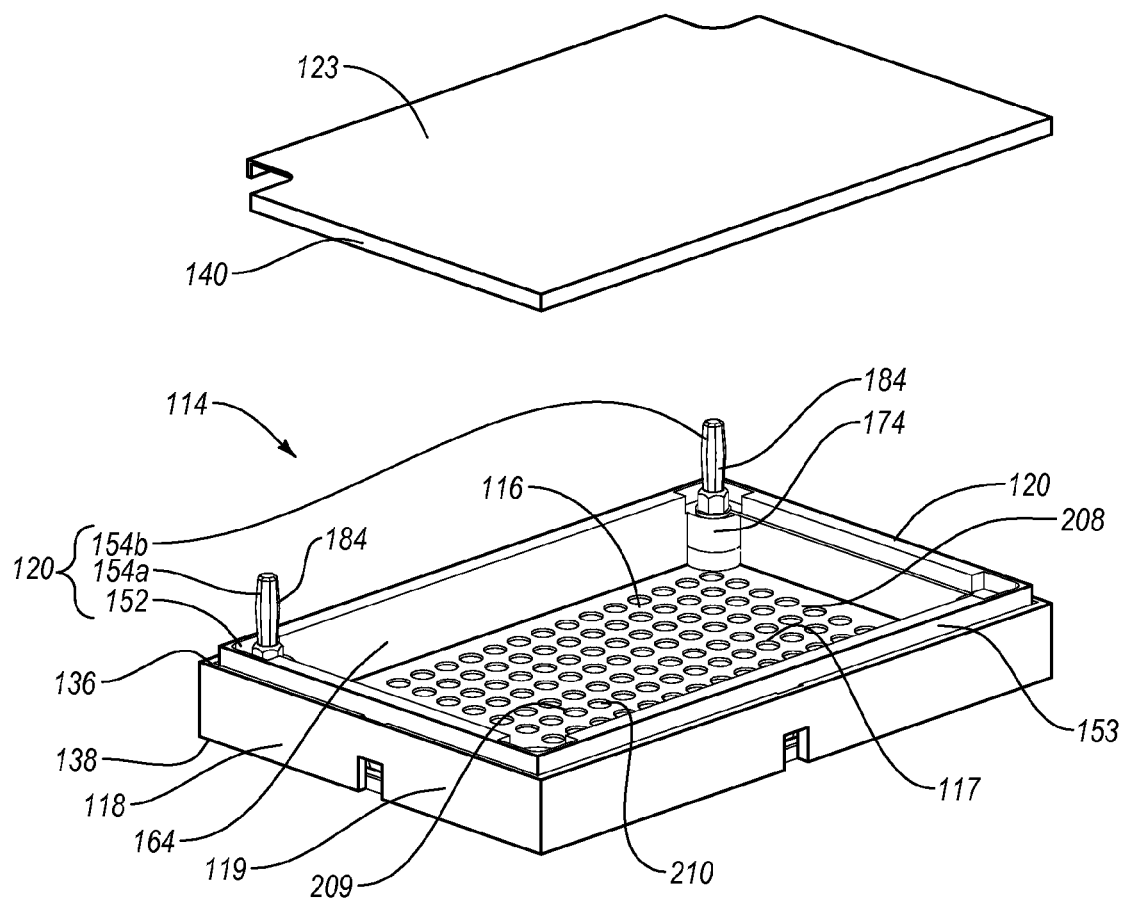
FIG. 2 is a perspective view of an assembled slide holder assembly and optional lid, with a slide secured therein.
Figure 3:
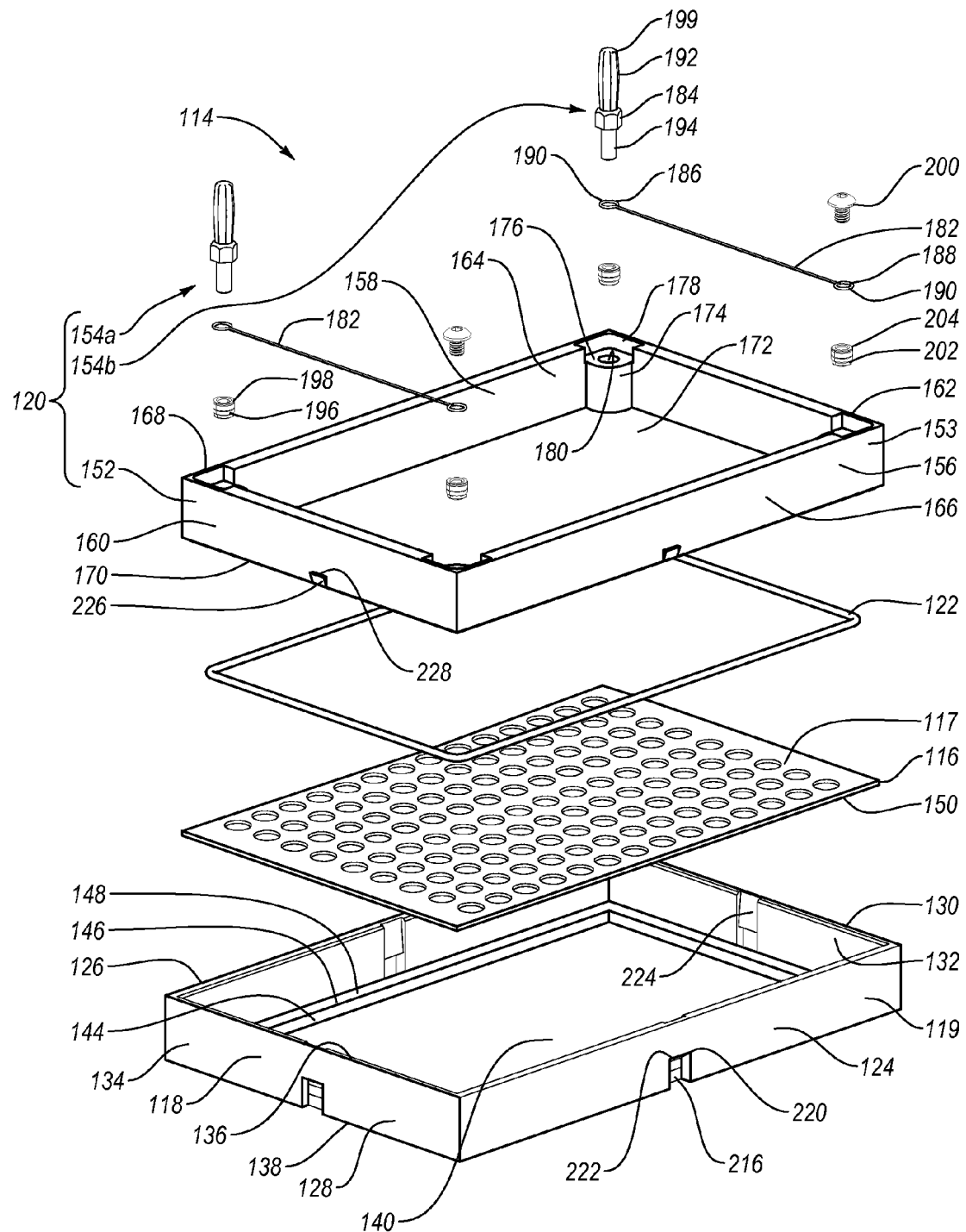
FIG. 3 is an exploded view of the slide holder assembly and corresponding slide shown in FIG. 2.

Turning to FIGS. 2 and 3, slide holder assembly 114 includes a slide holder 118, a slide cover assembly 120, a seal 122, and an optional lid 123. To perform an assay, slide 116 is first positioned within slide holder 118, then seal 122 and slide cover assembly 120 are positioned over slide 116 and secured within slide holder 118. Lid 123 can be placed over slide cover assembly 120 during all or part of an assay to protect the user from fluids used in the assay. In some embodiments, any or all of slide holder 118, slide cover assembly 120, seal 122, and lid 123 can be reusable, if desired.

Slide holder 118 is generally rectangular-shaped to match the shape of slide 116. Slide holder 118 has a perimeter sidewall 119 comprised of a front wall 124 and a back wall 126 extending between opposite first and second side walls 128 and 130. As such, perimeter sidewall 119 has an inside surface 132 and an opposing outside surface 134 that extend between a top surface 136 and an opposing bottom surface 138. Inside surface 132 bounds an opening 140 that extends completely through slide holder 118 between top and bottom surfaces 136 and 138.

Extending inward from inside surface 132 of perimeter sidewall 119 at or near the bottom end thereof is a slide support 144 that constricts opening 140. Slide support can form an inwardly facing flange that extends unbroken about the entire perimeter sidewall or can be broken into a plurality of flange segments. Slide support 144 has an upper surface 146 that forms a ledge 148 onto which a bottom surface 150 of slide 116 can be positioned. As such, the cross section of the portion of opening 140 above slide support 144 is larger than that of slide 116 so that slide 116 can be received within opening 140, and the cross section of the portion of opening 140 at slide support 144 is smaller than that of slide 116 so that slide 116 can rest on ledge 148 of slide support 144. When slide 116 is positioned on ledge 148, bottom surface 150 of slide 116 is openly exposed through the bottom portion of opening 140 of slide holder 118. If desired, an adhesive can be used to secure slide 116 to ledge 148, although this is not required. The adhesive can be permanent or removable.

Slide holder 118 can be sized to receive any size of slide used to perform a comet assay. For example, in the depicted embodiment, a standard 96-well slide is used and slide holder 118 is correspondingly sized. Other types and sizes of slides can also be used. For example, a slide having 2, 4, 20, 96, or 384 wells can be used. Other numbers of wells can also be used. Essentially, any slide format can be used, with slide holder being sized accordingly. In addition, although rectangular slides are generally used, other shapes can also be used, including regular and irregular shapes. In addition, as discussed below, slide holders can be designed to hold multiple slides, each slide having one or more wells.

Slide holder 118 can be comprised of metal, polymeric material, composites, or any other material that will support slide 116 therein. Additionally, slide holder 118 can be configured to be reusable, if desired.

Continuing with FIGS. 2 and 3, after slide 116 has been positioned within opening 140 of slide holder 118 so as to rest on ledge 148, slide cover assembly 120 can also be received within opening 148 to secure slide 116 between slide holder 118 and slide cover assembly 120. As such, slide cover assembly 120 is configured to be removably secured to slide holder 118 and to secure slide 116 therebetween. Slide cover assembly 120 comprises a slide cover 152 and a pair of electrical assemblies 154a and 154b attached thereto.

Slide cover 152 is configured to be snugly received within opening 140 of slide holder 118 and to be positioned above slide 116 after slide 116 has been positioned on ledge 148. As such, slide cover 152 is also generally rectangular-shaped, having a perimeter sidewall 153 comprised of a front wall 156 and a back wall 158 extending between opposite first and second side walls 160 and 162. Slide cover 152 is sized to be slightly smaller than opening 140 of slide holder 118 so as to be receivable therein. Perimeter sidewall 153 has an inside surface 164 and an opposing outside surface 166 that extend between a top surface 168 and an opposing bottom surface 170. Inside surface 164 bounds an opening 172 that extends completely through slide cover 152 between top and bottom surfaces 168 and 170. As such, when slide cover 152 is positioned within slide holder 118, opening 172 is aligned with opening 140. As a result, when slide 116 is positioned between slide holder 118 and slide cover 152, top surface 117 of slide 116 is openly exposed through opening 172 of slide cover, and, as noted above, bottom surface 150 of slide 116 is openly exposed through the bottom portion of opening 140 of slide holder 118.

Extending inward into opening 172 from the corners of slide cover 152 are protrusions 174 that provide platforms for securing electrical assemblies 154 thereto. Each protrusion 174 extends from or near bottom surface 170 of slide cover 152 to a top surface 176. In the depicted embodiment, top surfaces 176 of protrusions 174 are lower than top surface 168 of perimeter sidewall 153, although this is not required. A recess 178 is formed at each corner between top surface 176 of corresponding protrusion 174 and top surface 168 of perimeter sidewall 153. Protrusions 174 and recesses 178 are all generally cylindrically shaped; as a result, top surface 176 of each protrusion 178 is generally circular. Other shapes are also possible.

A bore 180 extends into top surface 176 of each protrusion 174 to receive a portion of the electrical assemblies 154, as discussed in more detail below. Each bore 180 can be threaded or unthreaded and can extend partially or entirely through the corresponding protrusion 174 to bottom surface 170 of slide cover 152.

Slide cover 152 can be comprised of similar types of materials as slide holder 118, discussed above. In some embodiments, slide cover 152 and slide holder 118 are comprised of the same material. Additionally, slide cover 152 can be configured to be reusable, if desired.

Continuing with FIGS. 2 and 3, the pair of electrical assemblies 154a and 154b are used to pass an electric current over slide 116 when slide 116 is secured within slide holder assembly 114, in effect forming a miniature electrophoresis chamber. Specifically, electrical assemblies 154 are configured to allow the electric current to flow therebetween, thereby causing an electric field to be formed above slide 116. As a result, slide holder assembly 114 can not only be used to perform lysis on the cells, but can also be used to electrophorese the cells. As such, electrical assemblies 154 are typically positioned on opposite ends of slide cover 152. For example, in the depicted embodiment, electrical assemblies 154a and 154b are positioned respectively on first and second side walls 160 and 162. The structure of electrical assemblies 154a and 154b are essentially identical in the depicted embodiment. Therefore, for ease of viewing, only the structural elements of electrical assembly 154b are labeled in FIG. 3, even though corresponding structural elements can be found on electrical assembly 154a. Each electrical assembly 154 comprises an electrode 182 secured to slide cover 152 and an electrical connector 184 electrically coupled to electrode 182.

Electrode 182 can comprise any electrical device that will transmit or receive an electrical current. To provide the electrical current across the entire width of slide 116, each electrode 182 can extend along the entire length of the side wall on which the electrode is positioned. For example, in the depicted embodiment, each electrode 182 comprises a wire extending along the corresponding side wall 160 and 162 between a first end 186 disposed on or near front wall 156 of slide cover 152 and a spaced apart second end 188 disposed on or near back wall 158 of slide cover 152. A loop 190 can be formed at each end 186 and 188 to help in attaching electrodes 182 to slide cover 152.

Electrode 182 can be comprised of stainless steel, platinum, or any other material known in the art, and can be bare or coated. For example, in the depicted embodiment, each electrode 182 can comprise a bare platinum wire. Alternatively, electrode 182 can comprise a conductive material, such as conductive paint, tape, paste or metal strip, that is painted on or otherwise adhered to side wall 160 or 162. In these embodiments, in place of a loop 190, the conductive material can be extended to the top surface 176 of protrusion 174 and into bore 180, if desired.

Electrical connector 184 can comprise a coupling portion 192 and a securing portion 194 extending therefrom. Securing portion 194 and coupling portion 192 can be separate and distinct discrete portions that are attached together, or can be integrally formed. In the depicted embodiment, securing portion 194 and coupling portion 192 are integrally formed. Securing portion 194 is inserted through loop 190 at first end 186 of electrode 182 and into bore 180 so that coupling portion 192 remains outside of bore 180. Securing portion 194 is secured within bore 180 such that electrical connector 184 makes a solid electrical connection with loop 190, or with the conductive material positioned on protrusion 174. An insert 196 can first be secured within bore 180, if desired, before securing portion 194 is secured within bore 180. If bore 180 or insert 196 has threads, securing portion 194 can have mating threads that allow securing portion 194 to be threadedly secured within bore 180. If bore 180 or insert 196 is not threaded, securing portion 194 can be press-fit or snap-fit within bore 180. An adhesive can be used alone or in conjunction with any of the other securing methods. One or more washers 198 can also be used to aid in securing and electrically coupling electrode 182 and electrical connector 184.

Coupling portion 192 of electrical connector 184 is used to attach to external electrical connectors that provide current to the electrical assemblies 154. As such, coupling portion 192 can comprise any electrical connector known in the art. For example, in the depicted embodiment, banana plugs 199 are used as the coupling portions 192 of electrical connectors 184. Other types of coupling portions, as are known in the art, can also be used. All or portions of electrical assemblies 154 can be configured to be reusable, if desired. In addition, some or all of each electrical assembly 154 can be incorporated into lid 123 instead of slide holder 118. For example, in one embodiment, coupling portion 192 of electrical connector 184 is positioned on lid 123 so as to electrically connect with the corresponding securing portion 194 secured to slide cover 152 when lid 123 is positioned over slide cover 152.

To secure the second end 188 of electrode 182 to slide cover 152, a fastener 200 can be used. Fastener 200 can be inserted through loop 190 at second end 188 of electrode 182 and into bore 180 positioned on the opposite side of slide cover 152 as electrical connector 184. Similar to that discussed above, an insert 202 can first be secured within bore 180, if desired, before fastener 200 is secured within bore 180. If bore 180 or insert 202 has threads, fastener 200 can have mating threads that allow fastener 200 to be threadedly secured within bore 180. If bore 180 or insert 202 is not threaded, fastener 200 can be press-fit or snap-fit within bore 180. An adhesive can be used alone or in conjunction with any of the other securing methods. One or more washers 204 can also be used to aid in securing second end 188 of electrode 182 to slide cover 152.

Fastener 200 can comprise a screw, a bolt, a snap fit connector, or other type of fastener known in the art. For example, in the depicted embodiment, screws are used as fasteners 200. Other fasteners, as are known in the art can also be used. Alternatively, electrode 182 can be secured by other non-fastening means. For example, in some embodiments, loop 190 at second end 188 of electrode 182 can be positioned over a post or the like (not shown) so that the tension between first and second ends 186 and 188 of electrode 182 causes second end 188 to remain on the post. If an alternative conductive material is used that is painted on or adhered to side wall 160 or 162, fastener 200 and its accompanying hardware may not be needed.

During use, an external power source is electrically connected to coupling portions 192 so that the circuit is completed through slide holder assembly 114. More particularly, the electrical current from the external circuit passes through the coupling portion 192 of a first one of the electrical connectors 184 to the corresponding electrode 182. The electrical current then passes through an electrophoresis solution covering the top surface 117 of slide 116 and to the second electrode 182. The electrical current from the second electrode 182 passes back to the external circuit through the coupling portion 192 corresponding to the second electrode 182. As such, one of the electrodes 182 will act as a cathode and the other electrode 182 will act as an anode.

To allow the electric current to pass over the length of slide 116, one electrical assembly 154 is typically attached to one side 160 of slide cover 152 and the other electrical assembly 154 is typically attached to the opposite side 162, as shown in FIG. 2. To produce a generally consistent level of electrophoresis across the width of slide 116, each electrode 182 can be positioned so that electrode 182 is an equal distance from the top surface 117 of slide 116 along the entire length of electrode 182. That is, each electrode 182 can be substantially parallel to the top surface 117 of slide 116, although this is not required. In addition, to produce a generally consistent level of electrophoresis across the length of slide 116, electrodes 182 can be an equal distance from each other. That is, electrodes 182 can be parallel to each other, although this is also not required. Electrodes 182 are generally positioned to be between about 0 mm to about 15 mm above slide 116 during use, with about 1 mm to about 4 mm being common. In some embodiments, electrodes 182 are positioned less than about 5 mm from the slide, while in other embodiments, electrodes 182 can contact the top surface 117 of slide 116. Other distances above slide 116 can also be used.

Figure 4:
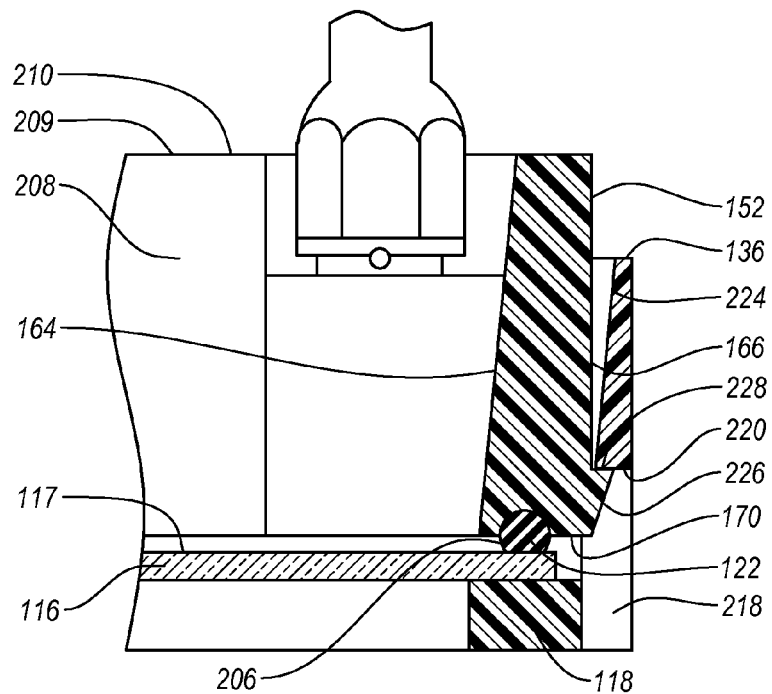
FIG. 4 is a cross sectional view of a portion of the assembled slide holder assembly and corresponding slide shown in FIG. 2.

Seal 122 is configured to be sandwiched between top surface 117 of slide 116 and bottom surface 170 of slide cover 152 so as to provide a substantially water-tight seal therebetween. As such, seal 122 generally matches the shape of slide cover 152. For example, in the depicted embodiment, seal 122 is generally rectangular to match slide cover 152. To provide a watertight seal, seal 122 can be pliable and compressible, if desired. As shown in FIG. 4, a groove or channel 206 can be formed on bottom surface 170 of slide cover 152 to aid in the positioning of seal 122, although this is not required. Seal 122 can be comprised of rubber, silicone, a polymeric material or any other sealing material known in the art. Additionally, seal 122 can be configured to be reusable, if desired. To aid in providing the watertight seal, slide cover 152 can be pressed against seal 122 by a pressing force. That is, slide cover 152 can be pressed against seal 122 with sufficient force to compress or otherwise seal 122 between bottom surface 170 of slide cover 152 and top surface 117 of slide 116, as shown in FIG. 4. As discussed above, an adhesive can be used to secure slide 116 to ledge 148, which can also aid in providing the watertight seal.

When seal 122 is secured between slide cover 152 and slide 122, inside surface 164 of slide cover 152 and top surface 117 of slide 116 combine to form a watertight cavity 208 having a mouth 209 at an open top end 210. As a result, the lysing reagent and electrophoresis buffer can be respectively poured into cavity 208 to lyse and electrophorese the cells positioned on top surface 117 of slide 116. Because cavity 208 can be small enough, if desired, to receive a solution that only covers top surface 117 of slide 116, the amount of lysing reagent and electrophoresis buffer respectively required for lysis and electrophoresis, as well as any other liquids used in cavity 208, can be greatly minimized.

Returning to FIGS. 2 and 3, to provide a sufficient force to sandwich seal 122 between slide 116 and slide cover 152, slide holder assembly 114 also includes means for removably securing slide cover 152 to slide holder 118. The means for removably securing slide cover 152 to slide holder 118 can comprise any securing system that will cause slide cover 152 to be secured to slide holder 118, yet allow slide cover 152 to be removed therefrom when desired. For example, in the depicted embodiment, the means for removably securing incorporates a snap-fit connection having mating portions on slide holder 118 and slide cover 152.

Returning to FIG. 4 in conjunction with FIGS. 2 and 3, corresponding to one portion of the snap-fit connection, a small opening 218 is formed on each wall 124, 126, 128, and 130 of slide holder 118 so as to extend through the wall. Each opening 218 has a downward-facing lip 220 at a top portion 222 thereof. A ramp 224 can be positioned between lip 220 and top surface 136 of slide holder 118 to aid in the snap-fit connection.

Corresponding to the other portion of the snap-fit connection, a tab 226 is positioned on outside surface 166 of each wall 156, 158, 160, and 162 of slide cover 152 so as to align with openings 218 when slide cover 152 is received within slide holder 118. Each tab 226 extends outward from outside surface 166 so as to form an upward-facing lip 228. When slide cover 152 is positioned within opening 218 of slide holder 118 and pushed downward over seal 122, tabs 226 contact ramps 224, which cause walls 156, 158, 160, and 162 of slide cover 152 to slightly flex inward or walls 124, 126, 128, and 130 of slide holder 118 to slightly flex outward, or both. Once tab 226 has completely passed downward beyond lip 220 of opening 218, the corresponding wall flexes back to its original orientation, causing tab 226 to be received within opening 218, as shown in FIG. 4. Lip 220 of opening 218 presses against lip 228 of tab 226, securing tab 226 within opening 218 and thereby compressing seal 122 between slide cover 152 and slide 116 and securing slide cover 152 to slide holder 118.

When it is desired to remove slide 116 from slide holder assembly 114, slide cover 152 is first removed from slide holder 118. To do so, slide cover 152 is pulled upward with respect to slide holder 118 with sufficient force to overcome the retention force causing tabs 226 to remain within openings 218. That is, slide cover 152 is pulled upward at a predetermined force that causes tabs 226 to move away from openings 218 so as to separate lips 220 and 228, thereby allowing slide cover 152 to be removed from opening 218 of slide holder 118. The force required to separate slide cover 152 from slide holder 118 is great enough so that slide cover 152 will not be inadvertently unsecured by forces that occur during normal use of slide holder assembly 114 when slide cover 152 is secured to slide holder 118. Once slide cover 152 is removed from opening 218, seal 122 and slide 116 can also be removed therefrom.

The snap-fit connection discussed above is only one type of means for removably securing slide cover 152 to slide holder 118 that can be used. Other types of snap-fit connections can also be used. For example, latches, threaded connections, press fit connectors, and the like can alternatively be used. Other types of securing devices and methods can also be used.

In an alternative embodiment, slide cover 152 can be permanently secured to slide holder 118. For example, slide cover 152 can be welded or otherwise permanently attached to slide holder 118 after slide 116 and seal 122 have been positioned therein.

Figure 5:
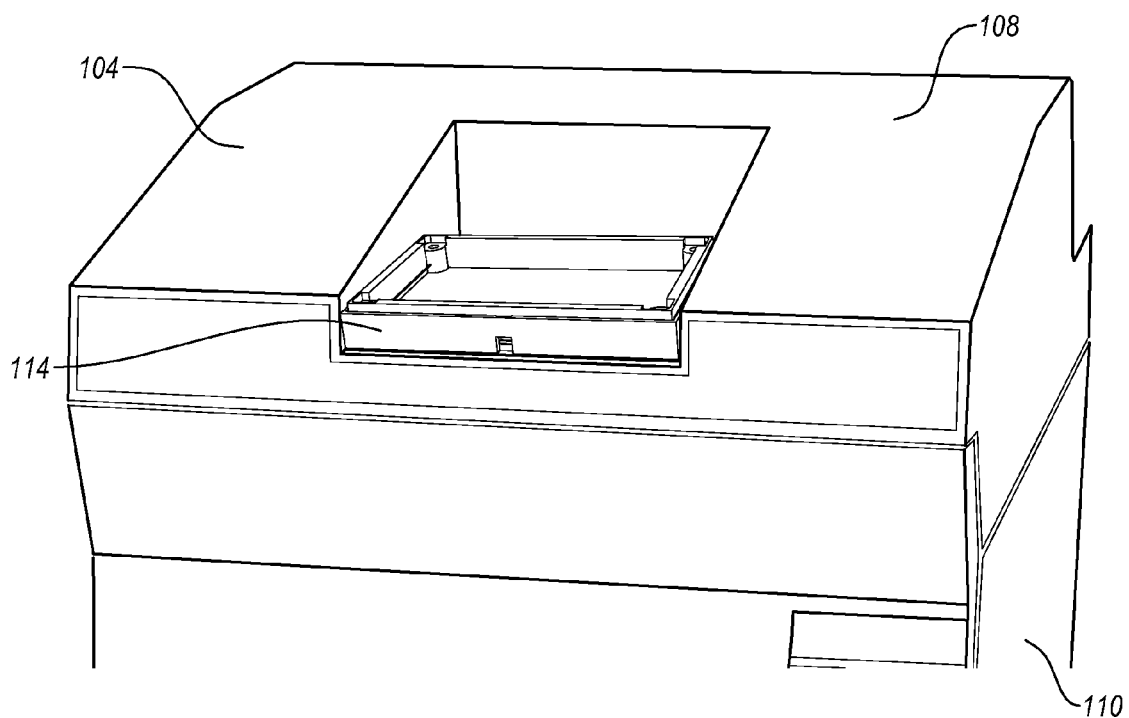
FIG. 5 is a perspective view of a slide holder assembly and corresponding slide being inserted into an imaging system.

When slide holder assembly 114 is assembled with slide 116 secured therein, slide 116 can be stained and slide holder assembly can be inserted into high-content cell imaging system 102 so slide 116 can be imaged therein. In some embodiments, the dimensions of the assembled slide holder assembly 114, with or without electrical connectors 184, may conform to standard SBS standards to be able to be received within imaging system 102. In some embodiments, electrical connectors 184 may need to be removed before slide holder assembly 114 can be positioned within imaging system 102, as shown in FIG. 5.

Returning to FIG. 2, lid 123 is sized to rest on slide cover 152 so as to cover opening 172. Lid 123 is typically used during electrophoresis, although lid 123 can be used at any time. Lid 123 is generally rectangular shaped and slightly longer and wider than slide cover 152. Lid 123 can be customized to fit on slide cover 152. For example, in the depicted embodiment, lid 123 has portions thereof cut out that would otherwise contact electrical connectors 184 and prevent lid 123 from resting on slide cover 152. As discussed above, in some embodiments some or all of each of the electrical assemblies can be incorporated into the lid instead of slide cover 152.

Lid 123 can include a downturned perimeter edge 240 to engage the outside surface 166 of perimeter side wall 153 at the top end thereof. Lid 123 can be designed so that perimeter edge 240 snap-fits onto slide cover 152. Alternatively, perimeter edge can be sufficiently wider and longer than slide cover 152 so that lid 123 can be placed on slide cover 152 without being secured to slide cover 152. Alternatively, lid 123 can be sized larger to also fit over the slide holder. This may be beneficial, for example, in embodiments where the slide cover does not extend above the top surface of the slide holder (see, e.g., FIG. 6). Lid 123 can be made of any type of material that will prevent a user from reaching into opening 172 when liquid is disposed therein and can be opaque or transparent or some combination thereof. To prevent electrical shorting, lid can be comprised of a non-conducting material, if desired.

Figure 6:
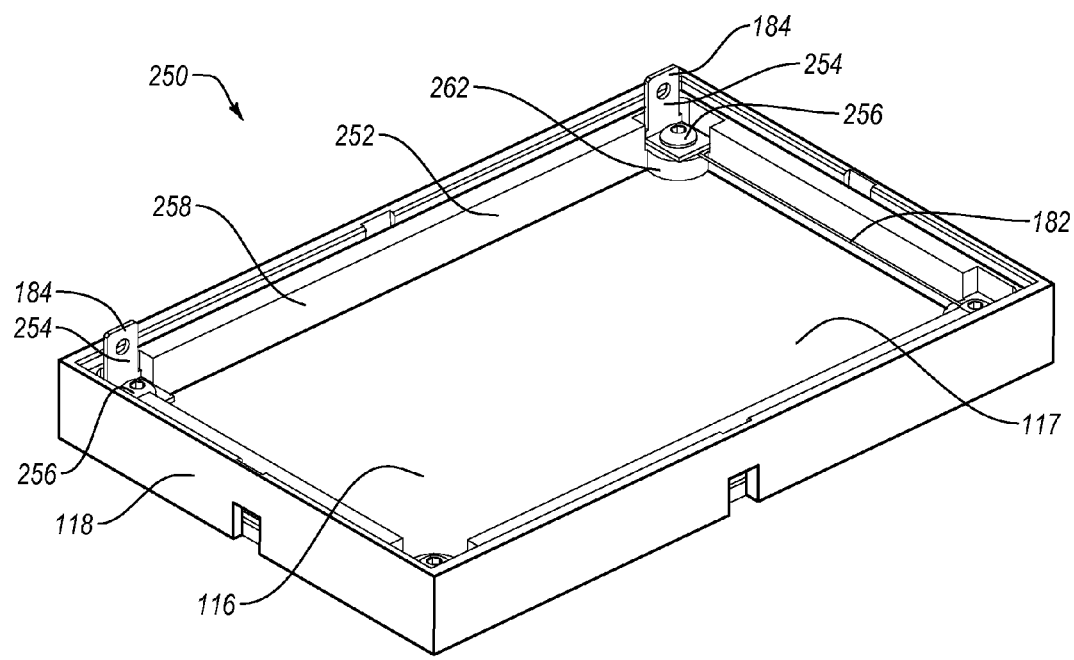
FIG. 6 is a perspective view of an assembled slide holder assembly with a slide secured therein according to an alternative embodiment.

FIG. 6 shows an alternative embodiment of a slide holder assembly 250 according to the present invention. Slide holder assembly 250 is similar to slide holder assembly 114 in that it also includes seal 122 (FIG. 3) and slide holder 118. A slide cover assembly 252 is also included that is similar to slide cover assembly 120 in many respects. However, instead of using banana plugs as electrical connectors 184, slide cover assembly 252 incorporates standard blade connectors 254, also commonly known as faston connectors, as the coupling portions. Furthermore, the securing portions of electrical connectors 184 comprise short screws 256 that are separate and discrete from blade connectors 254. Because of the change in electrical connectors 184, slide cover assembly 252 has a slide cover 258 having bores (not shown) and corresponding protrusions 262 that can be shorter than the bores 180 and protrusions 174 of slide cover 152. As a result, slide cover 258 can be substantially shorter than slide cover 152.

In addition, because protrusions 262 are shorter, electrodes 182 positioned therebetween can be positioned nearer to slide 116.

For some applications it may be desired to position electrodes 182 even closer to top surface 117 of slide 116 than can be attained by spanning electrodes 182 between the top surfaces of the protrusions. For example, in some applications, placing electrodes 182 closer to slide 116 will result in less current being required for electrophoresis and less heat to be generated. In those cases, one or more positioning aids can be used. Positioning aids are designed to position electrodes 182 at a predetermined position above slide 116.

Figure 7:
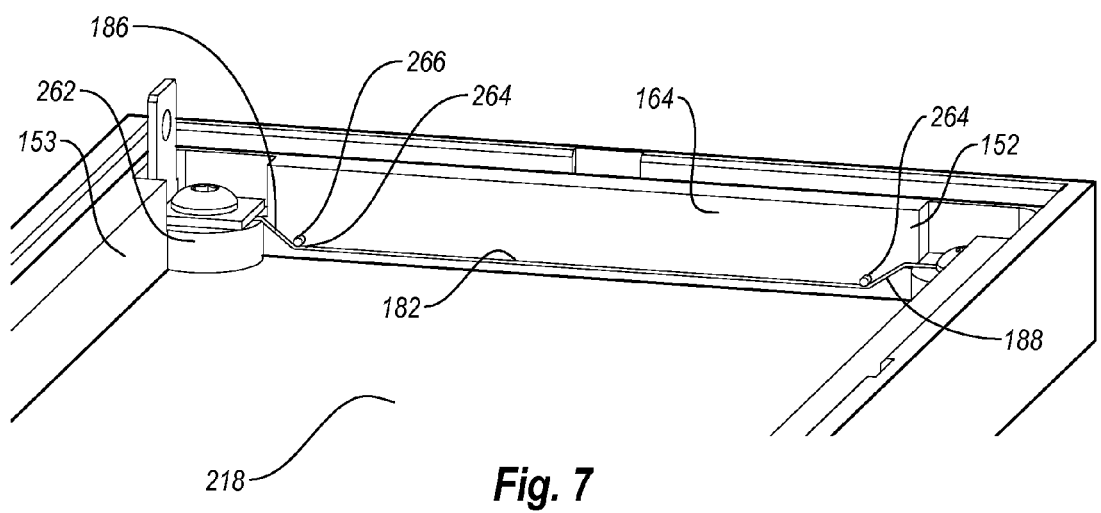
FIG. 7 is a cross sectional view of a portion of the assembled slide holder assembly and corresponding slide shown in FIG. 6, showing various electrode positions.
Figure 8:
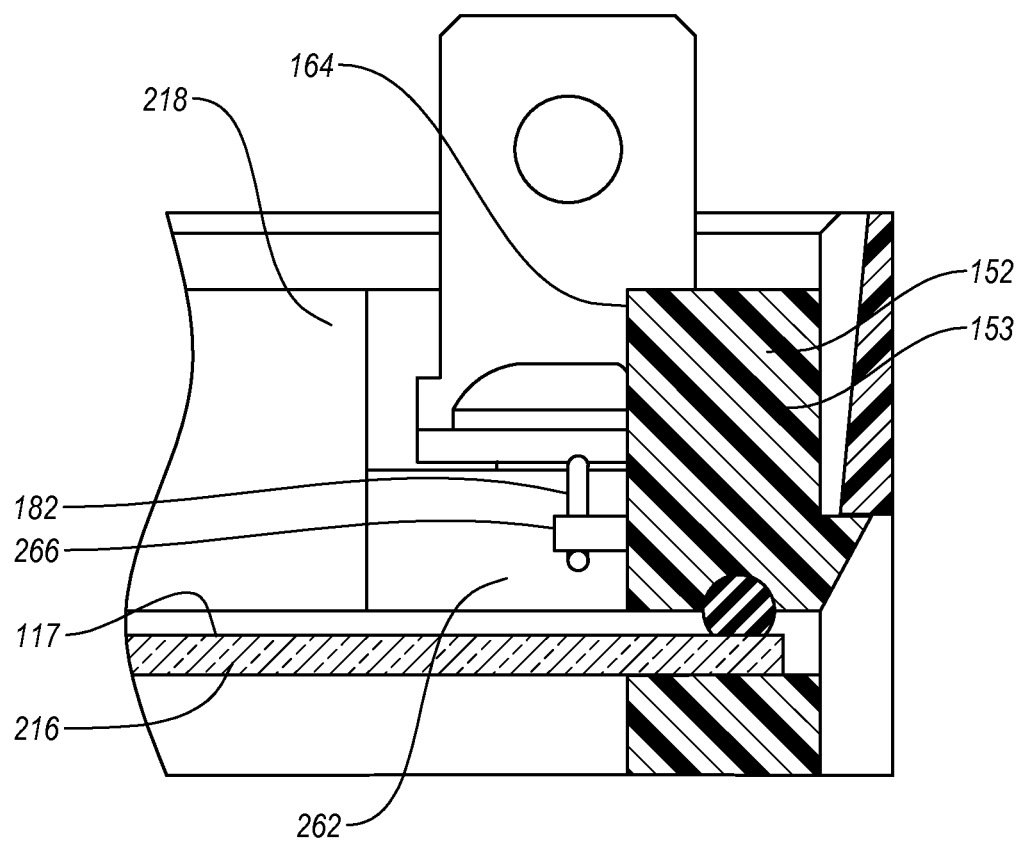
FIG. 8 is a cross sectional view of a portion of the assembled slide holder assembly and corresponding slide shown in FIG. 6.

Turning to FIGS. 7 and 8, a pair of positioning aids 264 are used to lower the center portion of electrode 182 below the level of protrusions 262. Positioning aids 264 can be formed on inside surfaces 164 of slide cover 152 or attached thereto. In addition, positioning aids 264 can be permanently attached to or formed with inside surfaces 164, or may be removable therefrom. In the depicted embodiment, each positioning aid 264 comprises a post 266 extending into opening 218 from inside surface 164 of slide cover 152. Each post 266 can be integrally formed with perimeter sidewall 153 or can be threaded, press-fit, or snap-fit into the wall. Alternatively, an adhesive can be used to attach post 266 to the wall. Other attachment methods can also be used.

Once both ends 186 and 188 of electrode 182 have been secured within slide cover 152, the center portion of electrode 182 can be manually moved below positioning aids 264. Positioning aids 264 then cause electrode 182 to remain in the lowered position until removed. In one embodiment using posts 266, electrode 182 was able to be positioned about 2 mm above surface 117 of slide 116.

Although only two posts 266 are shown in the depicted embodiment, it is appreciated that more posts can be used, if desired. For example, three, four, or more posts 266 can be used. Furthermore, it is appreciated that posts 266 are only one example of a positioning aid 264 that can be used. Other examples of positioning aids 264 that can be used include hooks, flanges and other devices, either attached to or integrally formed with perimeter sidewall 153. One or more grooves or channels can alternatively be formed within the inside surface 164 of slide cover 152. Other types of positioning aids can also be used.

Figure 13:
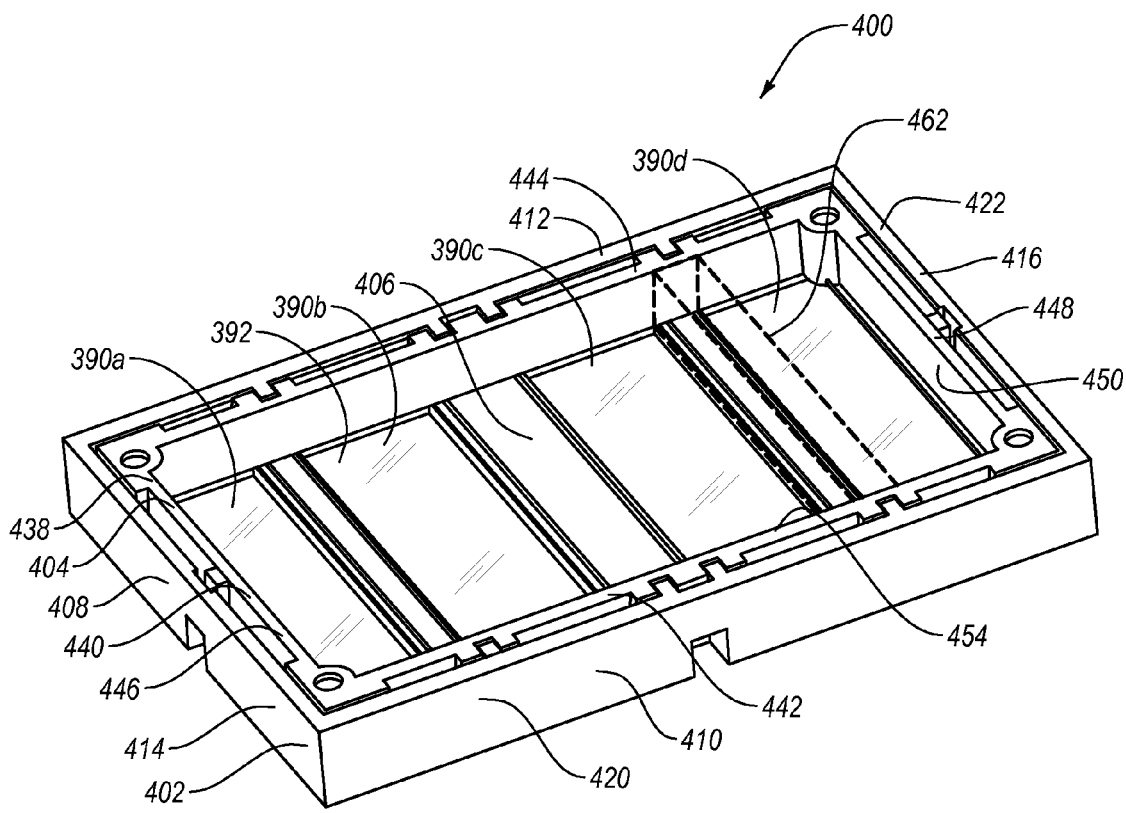
FIG. 13 is a perspective view of an assembled slide holder assembly with a plurality of slides secured therein according to another embodiment.
Figure 14:
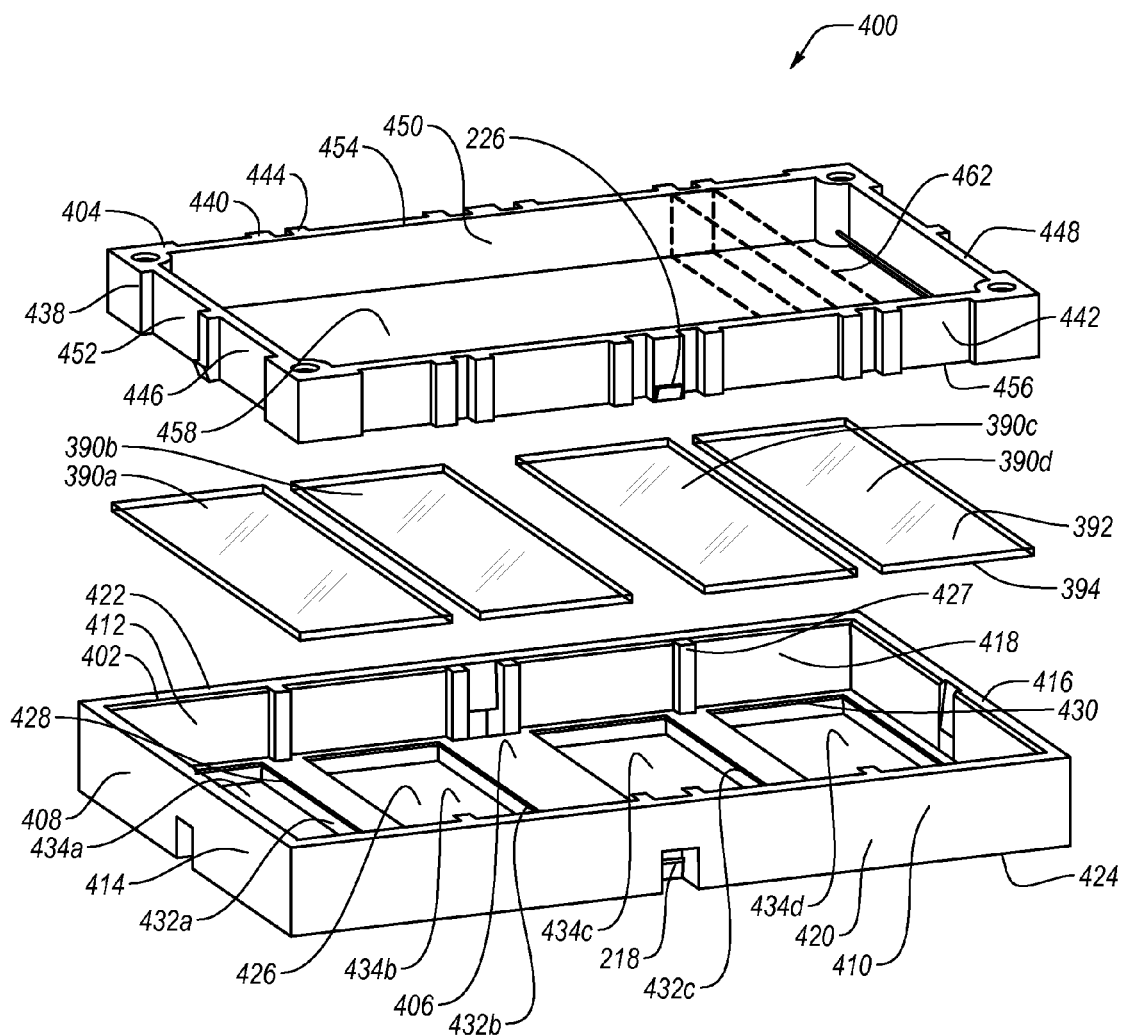
FIG. 14 is an exploded view of the slide holder assembly and corresponding slides shown in FIG. 13.
Figure 15:
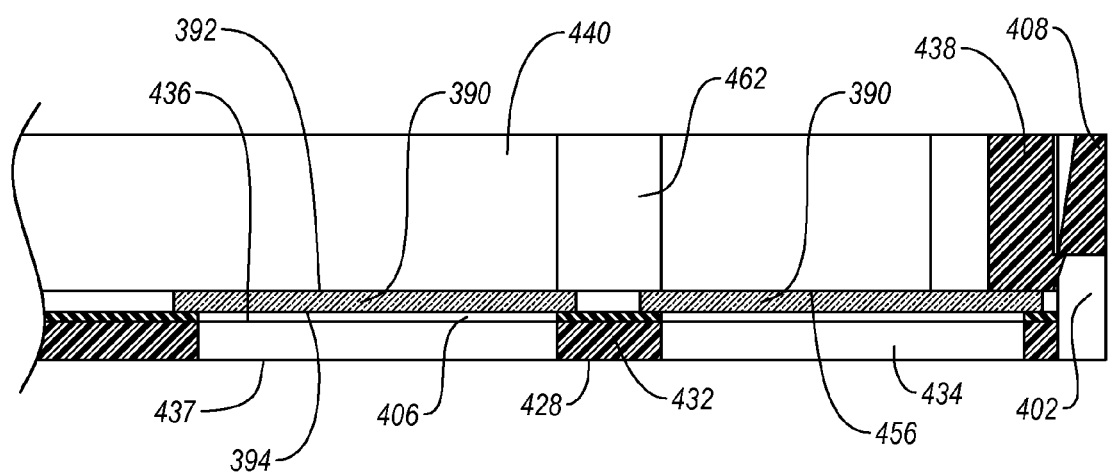
FIG. 15 is a cross sectional front view of a portion of the assembled slide holder assembly and corresponding slides shown in FIG. 13.

As noted above, slide holders can be designed to hold multiple slides. FIGS. 13-15 show one embodiment of a slide holder assembly 400 that is designed to hold four standard-sized microscope slides 390a-390d, each having a top surface 392 and an opposing bottom surfaces 394.

Similar to the embodiments discussed above, slide holder assembly 400 includes a slide holder 402 configured to receive a slide cover assembly 404 therein. However, instead of a removable seal being positioned above the slide, slide holder assembly 400 includes a seal 406 that is integrated into slide holder 402 and configured to be positioned below the slides.

Similar to the embodiments discussed above, slide holder 402 has a perimeter sidewall 408 comprised of a front wall 410, a back wall 412, and opposing first and second side walls 414 and 416 and has an inside surface 418 and an opposing outside surface 420 that extend between a top surface 422 and an opposing bottom surface 424. Inside surface 418 bounds an opening 426 that extends through slide holder 402 between top and bottom surfaces 422 and 424. If desired, slide holder 402 can have a plurality of spaced apart vertical ridges 427 extending into opening 426 from inside surface 418 of front and back walls 410 and 412. The distance between ridges 427 can be substantially the same as the width of slides 390 so as to provide a guide for positioning slides 390 within opening 426.

Also similar to the embodiments discussed above, slide holder 402 includes a slide support 428 comprising a flange 430 extending inward into opening 426 from inside surface 418 of perimeter sidewall 408 at or near the bottom end thereof. In the depicted embodiment, flange 430 extends unbroken about the entire perimeter sidewall 408.

Slide support 428 also includes a plurality of beams 432a-432c that extend laterally across opening 426 between the portions of flange 430 on front and back walls 410 and 412. Beams 432 can have a substantially similar width or can be of differing widths. In the depicted embodiment, the center beam 432b is wider than the beams 432a and 432c on either side thereof, while those beams are of a similar width.

Beams 432a-432c are spaced apart from each other so as to divide opening 426 into four separate smaller openings 434a-434d extending therethrough. Each opening 434 is sized to be slightly smaller than each of slides 390. That is, the length and width of each opening 434 is slightly less than the length and width, respectively, of each slide 390. In the depicted embodiment, openings 434a-434d are substantially the same size. In other embodiments, the openings can be of differing sizes if slides of differing sizes are used.

Slide support 428 has an upper surface 436 and an opposing lower surface 437 and is substantially rigid so as to support slides 390 thereon.

Seal 406 is positioned on upper surface 436 of slide support 428 and is configured to provide a watertight seal between slides 390 and openings 434. As such, seal 406 is disposed on upper surface 436 of slide support 428 at least around openings 434. In the depicted embodiment, seal 406 covers all of slide support 428. Seal 406 can be secured to upper surface 436 of slide support 428, e.g., by adhesive, or can be integrally formed therewith, e.g., by molding therewith. Seal 406 can be comprised of rubber or other type of flexible watertight material, similar to the materials discussed above with respect to seal 122.

Slides 390 are positioned within slide holder 402 so as to be positioned above openings 434 and rest on seal 406 about the periphery of the opening. If included with slide holder 402, vertical ridges 427 can be used as guides to properly position slides 390, Similar to the embodiments discussed above, slide cover assembly 404 comprises a slide cover 438 and a pair of electrical assemblies attached thereto. The electrical assemblies have been omitted from slide cover assembly 404 in FIGS. 13-15 for the sake of clarity. However, it is appreciated that any of the electrical assemblies discussed or envisioned herein can be used with slide cover assembly 404.

Similar to the slide covers discussed above, slide cover 438 is configured to be received within opening 426 of slide holder 402 and has a perimeter sidewall 440 comprised of a front wall 442 and a back wall 444 extending between opposite first and second side walls 446 and 448. Perimeter sidewall 440 has an inside surface 450 and an opposing outside surface 452 that extend between a top surface 454 and an opposing bottom surface 456. Inside surface 450 bounds an opening 458 that extends completely through slide cover 438 between top and bottom surfaces 454 and 456. As such, when slide cover 438 is positioned within slide holder 420, opening 458 is aligned with opening 426. As a result, when slides 390 are positioned between slide holder 402 and slide cover 438, top surfaces 392 of slides 390 are openly exposed through opening 458 of slide cover 438, and bottom surfaces 394 of slides 390 are each openly exposed through openings 434 of slide support 428.

Similar to the slide cover assemblies discussed above, slide cover 438 is configured to aid in providing a watertight seal for slide holder assembly 400. Because seal 406 is positioned below slides 390, however, slide cover 438 is configured to push slides downward against seal 406, instead of vice versa. To provide the necessary downward force, slide cover 438 includes means for removably securing slide cover 438 to slide holder 402. The means for removably securing slide cover 438 to slide holder 402 can comprise any of the means discussed above. In the depicted embodiment, the means comprises a snap-fit connection having tab 226 on slide cover 438 and opening 218 on slide holder 402, similar to that discussed above.

Slide cover 438 can be comprised of the same type of materials discussed above regarding slide cover 152. To aid in providing the watertight seal, at least a portion of slide cover 438 can be comprised of a flexible material, such as rubber or the like. For example, the bottom surface 456 of slide cover 438 can be comprised of a rubberized material so as to seal against slides 390 when secured to slide holder 402. As another example, a rubber flange can surround tab 226 to seal against opening 218 when tab is secured therein, if desired.

One or more interior walls, denoted by dashed lines 462, can be included in slide cover 438 if needed to also directly apply the downward force to the edges of the interior slides 390. Interior walls can extend between front and back walls 442 and 444 and can be aligned with beams 432 so as to overlap the edges of slides 390 and thereby provide the downward force against slides 390. Interior walls 462 can extend all the way from bottom surface 456 of slide cover 438 to top surface 454 or a portion thereof. Lateral gaps and/or throughholes can be formed at the bottom of interior walls 462 to allow the various fluids and electrical current to flow through walls 462 between slides 390.

It is appreciated that slide holder assembly 400 is but one example of a slide holder assembly that can be used with multiple slides. For example, slide holder assembly 400 can be modified to be used with fewer or more than four slides. In addition, slide holder assembly can be modified to be used with different sized slides. Other modifications can also be made to be used with multiple slides. Furthermore, the concepts of slide holder assembly 400 can be incorporated into a slide holder assembly that only uses one slide. For example, slide holder assembly 114 can be modified so that a seal is positioned on slide support 144 instead of or in conjunction with seal 122. Other modifications can also be made.

In another embodiment that can be used with multiple slides, a clear floor can be positioned so as to rest on the slide holder in a similar manner as the slide does in the single slide embodiment discussed above. The multiple slides can then be positioned on top of the clear floor. The seal and slide cover assembly can then be positioned on the clear floor as if it were the single slide of the single slide embodiment. The top of the clear floor combines with the seal and the inside surface of the slide cover to form the watertight cavity. By virtue of being on top of the clear floor, the plurality of slides are within the watertight cavity. As such, the plurality of slides can be processed without having to use the seal underneath them that transverses the cavity.

Figure 9:
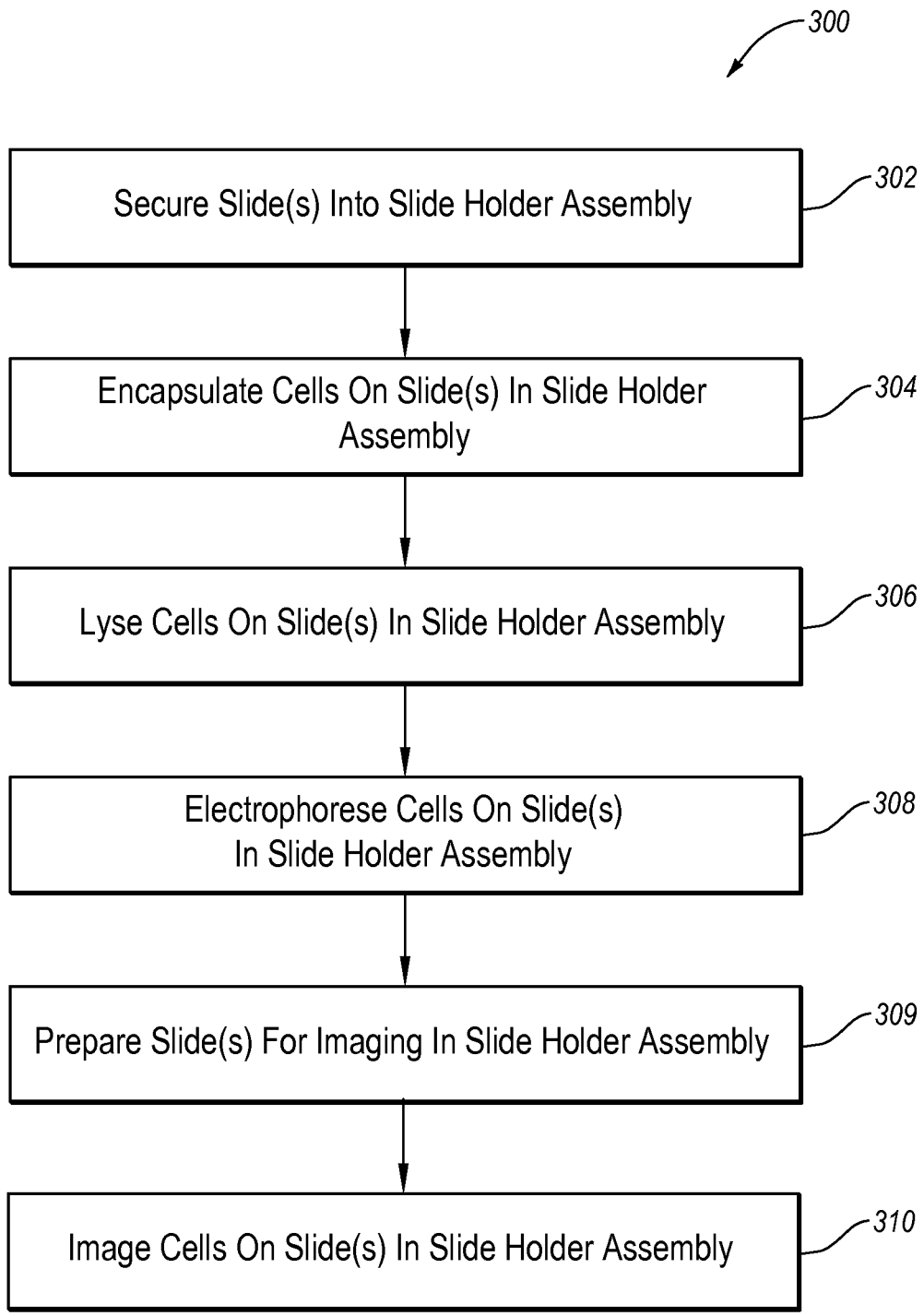
FIG. 9 is a flow diagram illustrating a method for performing a comet assay according to one embodiment.

As noted above, the slide holder assemblies disclosed or envisioned herein can be used in performing a comet assay. For example, FIG. 9 is a flow diagram illustrating one embodiment of a method 300 of performing a comet assay using any of the slide holder assemblies herein described. In the first step, denoted as step 302, the slide is secured within the slide holder assembly. Next, in steps 304, 306, 308, 309, and 310, the cells are encapsulated on the slide, caused to lyse, subject to electrophoresis, stained, and imaged, all while the slide remains secured within the slide holder assembly. In one embodiment, the encapsulation of the cells on the slide can be performed before the slide is secured within the slide holder assembly.

For purposes of clarity, the steps of method 300 will be discussed referring to slide holder assembly 114 shown in FIGS. 2 and 3. However, it is appreciated that this is exemplary only and that method 300 can be performed using any of the slide holder assemblies described or otherwise envisioned herein. At step 302, slide 116 can be positioned within opening 140 of slide holder 118, then seal 122 can be placed on top surface 117 of slide 116. Slide cover 152 can then be positioned on seal 122 and slide 116 and secured to slide holder 118, as discussed above. In this manner, a liquid-tight seal can be formed between top surface 117 of slide 116 and inside surface 164 of slide cover 152 so as to form cavity 208 with mouth 209 at the top end 210 thereof, also as discussed above.

At step 304, a sample of cells, either derived from an in vitro cell culture or from an in vivo test subject, can be dispersed into individual cells and suspended in molten low-melting-point agarose, as is known in the art. This mono-suspension can be cast on slide 116. A glass cover slip can be held at an angle and the mono-suspension applied to the point of contact between the cover slip and slide 116, as is known in the art. As the cover slip is lowered onto slide 116 the molten agarose spreads to form a thin layer. The agarose can then be gelled by cooling and the cover slip removed, as is known in the art.

The agarose forms a matrix of carbohydrate fibers that encapsulate the cells, anchoring the cells in place. The agarose is considered to be osmotic-neutral, therefore solutions can penetrate the gel and affect the cells without the cells shifting position. In an in vitro study, the cells can be exposed to a test agent, such as, e.g., UV light, ionizing radiation, or a genotoxic chemical, if desired, to induce DNA damage in the encapsulated cells.

At step 306, a solution that causes the cells to lyse is poured into cavity 208 through mouth 209 to cover top surface 117 of slide 116. This lysis solution, also known as a lysing reagent, is left in cavity 208 to cover slide 116 for a predetermined period of time, as is known in the art (e.g., 1-2 hours). If desired, lid 123 can be positioned over mouth 209 during the predetermined period of time to prevent anyone from inadvertently coming into contact with the lysis solution. In one exemplary embodiment, the lysis solution can comprise a highly concentrated aqueous salt (such as, e.g., common table salt) and a detergent (such as, e.g., $C_{14}H_{22}O(C_2H_4O)_n$ [also commonly known as Triton® X-100™] or sarcosinate). Other lysis solutions, as are known in the art, can also be used. The pH of the lysis solution can be adjusted (usually between neutral and alkaline pH) depending upon the type of damage that is being investigated.

The aqueous salt disrupts proteins and corresponding bonding patterns within the cell as well as the DNA content of the cell. The detergent dissolves the cellular membranes. Through the action of the lysis solution, the cells are essentially destroyed. The proteins, DNA, membranes and cytoplasmic and nucleoplasmic constituents are disrupted and diffuse into the agarose matrix. Only the DNA of the cell remains, and unravels to fill the cavity in the agarose that the whole cell formerly filled. This structure is called a nucleoid (a general term for a structure in which DNA is concentrated).

After the predetermined period of time, lid 123, if used, is lifted from mouth 209, the lysis solution is removed from cavity 208 (e.g., by aspiration) and, if desired, distilled water is poured into cavity 208 and then removed therefrom, to remove any remaining salts from slide 116. Because the lysis solution only must cover top surface 117 of slide 116, the volume of solution required is significantly less that that required in conventional assay systems. For example, in one embodiment, about 40 ml of lysis solution was used in contrast to the up to one liter or more required for conventional lysis containers. This results in less lysis solution in need of disposal after use, which helps the environment. A significant cost savings is also realized as a result of the lower volume of solution needed.

At step 308, an electrophoresis buffer solution, as is known in the art, is poured into cavity 208 through mouth 209 to cover top surface 117 of slide 116, and an external power source (not shown) is connected to slide holder assembly 114 to electrophorese the cells on slide 116. If desired, the slide can soak within the electrophoresis buffer for a predetermined period of time, as is known in the art, before the power source is connected, although this is not required. If desired, lid 123 can be positioned over mouth 209 during electrophoresis (and during the soaking period, if used) to prevent anyone from inadvertently coming into contact with the electrophoresis solution or the electrodes.

To connect the external power source to slide holder assembly 114, oppositely charged connectors of the power source are electrically connected to coupling portions 192 of electrical connectors 184, as discussed above, and the external power source is energized. Electrodes 182 become oppositely charged, thereby causing an electric field to pass through the cells between the electrodes. The strength of the electric field can be any strength known in the art for electrophoresing cell structures (e.g., 1 V/cm). The electric field is applied for a predetermined period of time, as is known in the art (for example, 20 minutes). The process of electrophoresis causes the DNA double helix to be denatured and any damaged strands to migrate After the predetermined period of time, the external power source is turned off and the external connectors can be disconnected from coupling portions 192 of electrical connecters 184. Lid 123, if used, is lifted from mouth 209, the electrophoresis buffer solution is removed from cavity 208 (e.g., by aspiration) and, if desired, distilled water is poured into cavity 208 and then removed therefrom, to remove any remaining electrophoresis buffer from slide 116. If desired, an ethanol mixture can also be poured into cavity 208 and then removed therefrom. Similar to the lysis solution discussed above, because the electrophoresis buffer solution (and ethanol mixture, if used) must only cover top surface 117 of slide 116, the volume of solution required is significantly less than that required in conventional assay systems. For example, in one embodiment, about 40 ml of electrophoresis buffer solution and about 15 ml of ethanol mixture were used in contrast to the up to 1 liter or more of each solution required for conventional electrophoresis chambers. This results in a significant cost savings, especially when performing a large number of comet assays. In addition, the present approach is less harmful on the environment because there is less solution in need of disposal after use.

At step 309, a staining solution is poured into cavity 208 through mouth 209 to cover top surface 117 of slide 116. The staining solution can contain a DNA-specific fluorescent dye that is absorbed by the cells on slide 116. Alternatively, the staining solution can contain other types of fluorescent dyes, if desired. The staining solution is left in cavity 208 to cover slide 116 for a predetermined period of time, depending on the dye used, as is known in the art. The staining solution is then removed from cavity 208 (e.g., by aspiration), and the slide is allowed to dry.

At step 310, slide holder assembly 114, with stained slide 116 secured therein, is then loaded into high content cell imaging system 102, such as one of those discussed above. The cells are then imaged using the microscope objective of microscope assembly 110 of cell imaging system 102, and analyzed using image analysis software, as is known in the art. If required, electrical connectors 184 can be removed from slide cover 152 before slide cover assembly 120 is loaded into imaging system 102.

If a comet assay is to be performed on more than one slide, the above method can be duplicated for each slide. In addition, in some embodiments, some or all of the slide holder assembly 114 can be reused to perform additional assays. Furthermore, because the slide remains secured within the slide holder assembly, all or some of the steps of the above method can be performed automatically. For example, a robot can perform most, if not all, of the steps recited herein. If more than one slide is to be assayed, the robot can perform the assays in order. In addition, multiple slide holder assemblies containing electrodes could be stacked in a hotel having individual connectors for each assembly. This would allow for electrophoresing many slides simultaneously.

Figure 10:
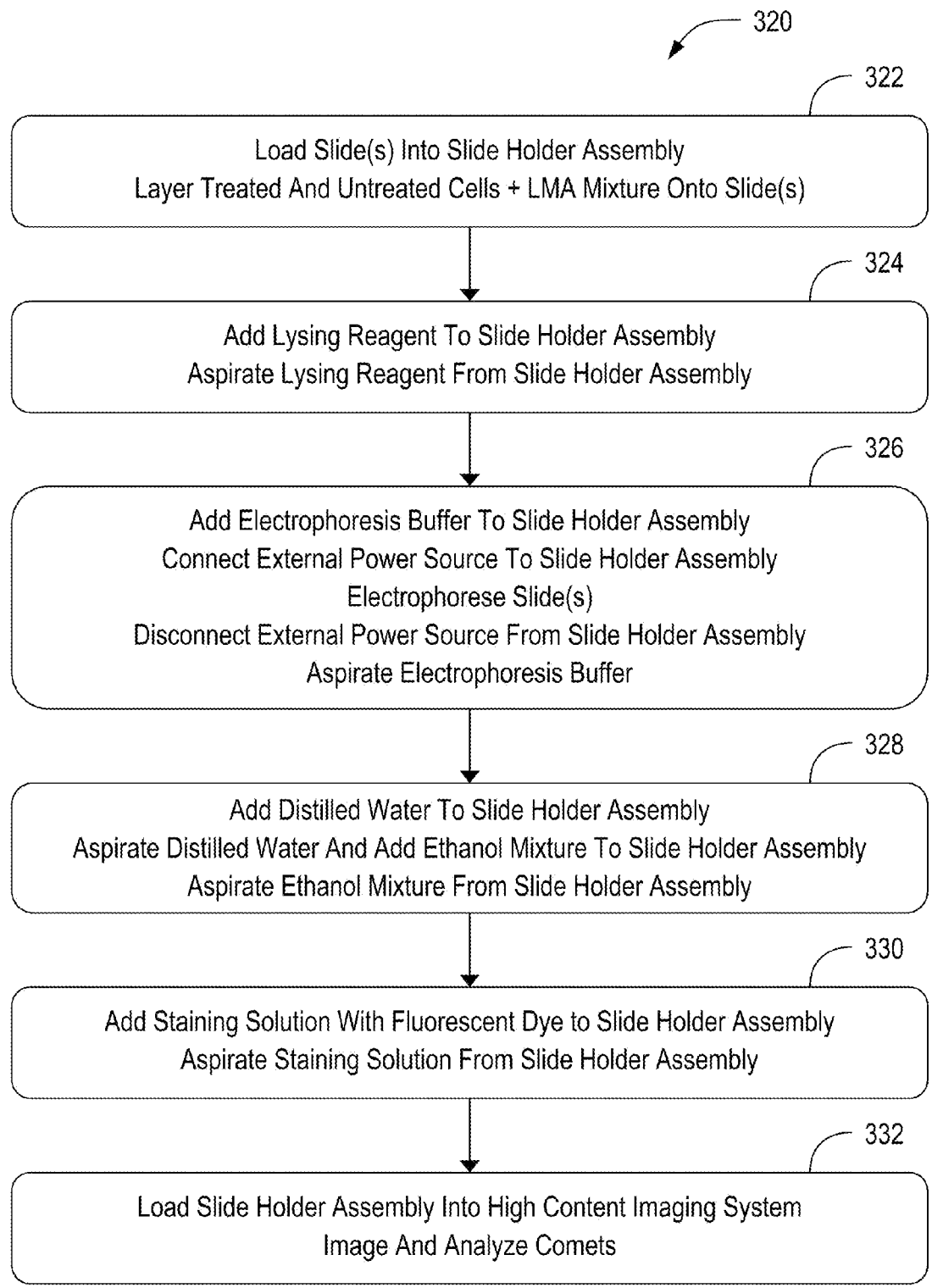
FIG. 10 is a flow diagram illustrating a method for performing a comet assay according to another embodiment.

FIG. 10 is a flow diagram illustrating another embodiment of a method 320 of performing a comet assay. For purposes of clarity, the steps of method 320 will be discussed referring to slide holder assembly 114 shown in FIGS. 2 and 3. However, it is appreciated that this is exemplary only and that method 320 can be performed using any of the slide holder assemblies described or otherwise envisioned herein.

At step 322, slide 116 is loaded into slide holder assembly 114, and the treated and untreated cells and LMA mixture are layered onto slide 116.

At step 324, a lysing reagent is added to slide holder assembly 114 so as to cover top surface 117 of slide 116. After a predetermined period of time, the lysing reagent is aspirated from slide holder assembly 114.

At step 326, an electrophoresis buffer is added to slide holder assembly 114 so as to cover top surface 117 of slide 116. An external power source is then connected to slide holder assembly 114 through electrical connectors 184. Slide 116 is electrophoresed for a predetermined period of time, as discussed above, after which the external power source is disconnected from slide holder assembly 114. The electrophoresis buffer is then aspirated from slide holder assembly 114.

At step 328, distilled water is added to slide holder assembly 114 so as to cover top surface 117 of slide 116. The distilled water is then aspirated from slide holder assembly 114 and an ethanol mixture is added to slide holder assembly 114 so as to cover top surface 117 of slide 116. In one embodiment, the ethanol mixture can be about 70% ethanol. Other ethanol percentages can also be used. The ethanol mixture is then aspirated from slide holder assembly 114.

At step 330, a staining solution is added to slide holder assembly 114 so as to cover top surface 117 of slide 116. The staining solution contains a fluorescent dye that is absorbed by the cells on slide 116. After a predetermined period of time, the staining solution is aspirated from slide holder assembly 114 and slide 116 is allowed to dry.

At step 332, slide holder assembly 114 is loaded, either manually or robotically, into a high content imaging system, such as those listed above. The comets are then imaged and analyzed using the high content imaging system.

As noted above, although the above methods refer to slide holder assembly 114 and its elements, it is appreciated that this is by example only and that any of the slide holder assemblies and corresponding elements disclosed or envisioned herein can alternatively be used.

Embodiments of the present invention provide many benefits over conventional assaying systems. For example, by using a common slide holder assembly to hold the slide through the different steps of a comet assay, there is no need for a separate electrophoresis chamber, washing chamber, staining chamber and imaging frame. Furthermore, by forming a cavity that only includes the top surface of the slide and the side surfaces of the slide cover, volumes of lysing reagents, electrophoresis buffers, and ethanol used in the processing of comet slides are greatly reduced. In addition, the ability to use robotic handling of processed comet slides into an automated high content analysis instrument allows for ultra-high throughput screening of genotoxic compounds.

Exemplary comet assays were performed using the above devices and methods. For example, in one comet assay, comets were successfully generated and analyzed using CHO-K1 cells on a 96-well glass slide. To ensure that comets would be produced, half of the CHO-K1 cells were treated with 100 μM 9-aminoacridine for one hour. A 96-well glass slide was secured within a slide holder assembly and half of the slide was layered with the treated CHO-K1 cells while the other half was layered with untreated CHO-K1 cells. The cells were allowed to soak in a lysis solution and then an electrophoresis buffer while in the slide holder assembly. The cells were then electrophoresed while in the slide holder assembly and then imaged using the ToxInsight IVT platform.

Figure 11:
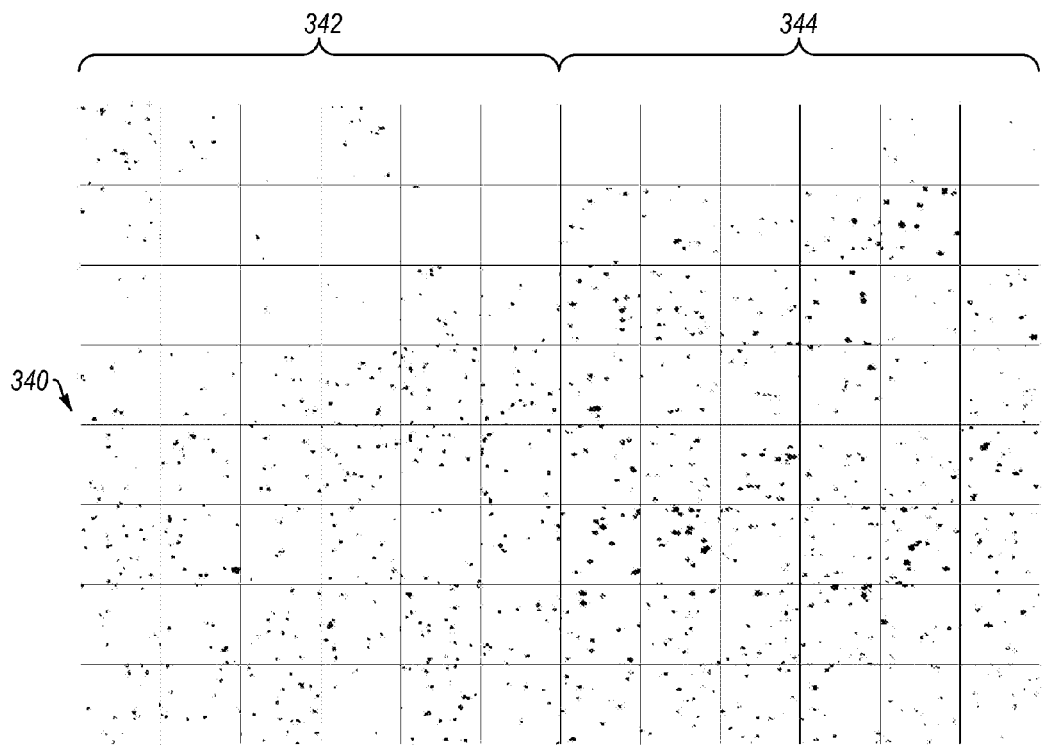
FIG. 11 is an image of a 96-well slide showing untreated CHO-K1 cells (on the left side) and treated CHO-K1 cells (on the right side) after performing a comet assay using a slide holder assembly.

FIG. 11 shows a composite image 340 of the glass slide showing the results of the sample comet assay. In FIG. 11, the untreated CHO-K1 cells 342 are shown in columns 1-6 (i.e., the left half of the image) and the treated CHO-K1 cells 344 are shown in columns 7-12 (i.e., on the right half). As expected, comets were formed and imaged on the treated cells 344 while generally not found on the untreated cells 342. In the sample comet assay, the ToxInsight® IVT Platform was used as the cell imaging system to scan 25 fields/well. Using the Comet.V4 BioApplication software developed by Cellomics Inc., 14,075 comets were automatically selected by the cell imaging system within a time period of 20 minutes, 29 seconds. Extrapolating, if electrified racks holding ten slide holder assemblies each were to electrophorese the slides contained therein simultaneously, it would be possible to analyze seventy two 96-well glass comet slides in a 24-hour day. This translates to over one million comets that could be analyzed per 24-hour day.

Figure 12:
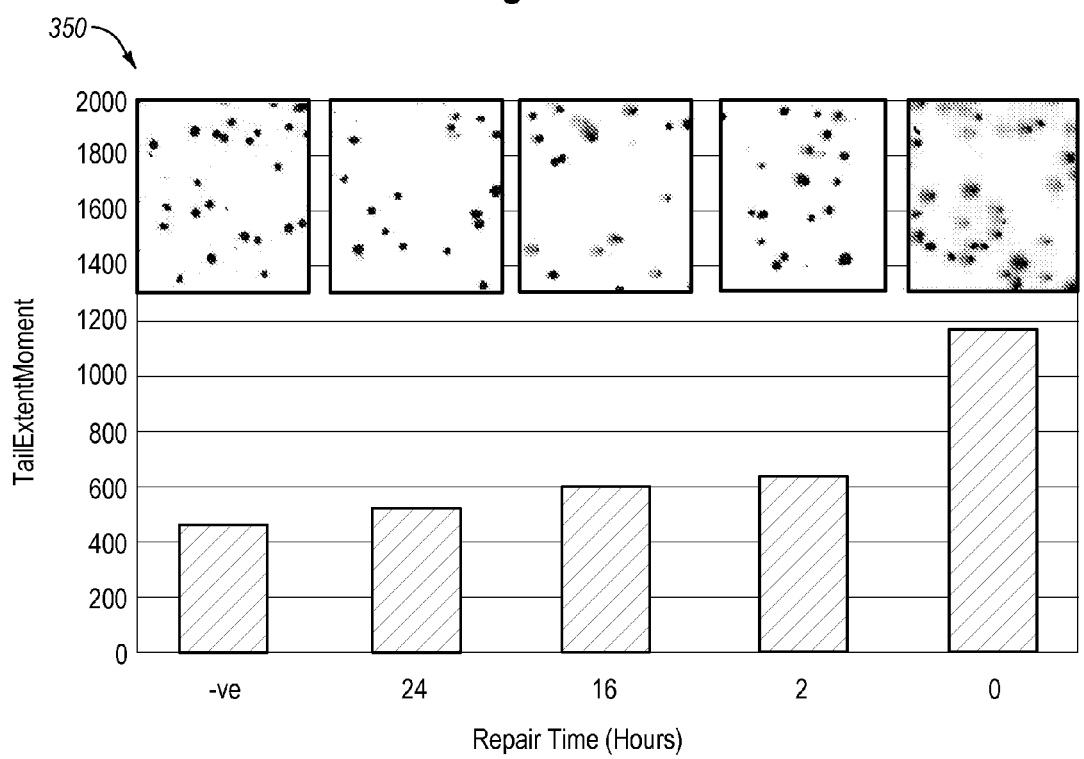
FIG. 12 is a composite image showing a graph of observed DNA repair and corresponding imaged cell comets at various repair times using a slide holder assembly.

In another sample comet assay, CHO-K1 cells were treated with 9-aminoacridine and the treated cells were layered onto select wells on the glass slide for varied durations of time. The cells were allowed to soak in a lysis solution and then an electrophoresis buffer while in the slide holder assembly. The cells were then electrophoresed while in the slide holder assembly and then imaged using the ToxInsight IVT Platform. This revealed a time-dependent response of DNA repair quantified in comets electrophoresed and imaged in the slide holder assembly. FIG. 12 shows the time dependent response 350 of DNA repair generated from the 96-well comet slide.

As noted above, the slide holder assemblies disclosed and envisioned herein are generally rectangularly shaped to match the shape of the slide that is secured therein. It is appreciated that slide holder assemblies of the present invention can conform to other shapes, if desired. For example, if slides are used that are circular, oval, square, or any other regular or irregular shape, the slide holder assembly can be designed to match the shape. In addition, the slide holder assembly may be differently shaped than the slide, if desired.

The discussion above has been directed toward using the slide holder assemblies in such a manner that various phases of the assay are performed by hand. For example, the steps of lysing and electrophoresing the cells are typically done by hand, external to the imaging system. The slide holder assembly is inserted into the imaging system for automated imaging only after the slide(s) have been prepared for imaging. This is only one way of using the slide holder assembly.

In an alternative embodiment, the various steps of the assay can be automated using slide holder assemblies according to the present invention. For example, one or more mechanical robots can be used to add the various liquids to the slide holder assemblies and aspirate the liquids therefrom. Mechanical robots can also be used to connect and disconnect the external electrical connectors and provide electrical current thereto for electrophoresis.

In one embodiment, the slide holder assembly and associated slide(s) can be positioned within an assay system that automatically performs all or some of the assay steps typically performed by hand. For example, one automated assay system includes a variable power source, an automatic liquid dispenser, an automatic liquid aspirator, and an automated imaging system. The assay system can also include one or more robots, as needed. Once the slide(s) is(are) secured to the slide holder assembly, the slide holder assembly can be positioned within the automated assay system, which performs all or some of the manual steps of the Comet AssayIn one embodiment, the automated assay system is housed in a single housing and the slide holder assembly is inserted into the housing through a slot or other opening on the housing. For example, in one embodiment, an automated imaging system can be modified to automatically perform the manual phases of the assay, along with imaging, analysis, and data visualization. The automated imaging system can be liquid-tight and electrically isolated. To perform electrophoresis, a variable power supply can be added to the imaging system, along with the capability to aspirate and dispense electrophoresis reagents. A robotic mechanism can also be added to the imaging system, if not already present, to maneuver and place the slide holder. In this manner, an automated imaging system having all the functionality of a fully automated high content analysis (HCA) imaging instrument can be used to accomplish electrophoresis of samples for the comet assay and various other gel electrophoresis assays from beginning to end including imaging, analysis and data visualization.

The present invention may be embodied in other specific forms without departing from its spirit or essential characteristics. Accordingly, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A slide holder assembly for use in high-content screening, the slide holder assembly configured to receive a slide holding a plurality of biological cells, the slide having a top surface and an opposing bottom surface, the slide holder assembly comprising:
    a slide holder having a perimeter sidewall with a top surface and an opposing bottom surface, an inside surface extending between the top and bottom surfaces of the sidewall so as to bound an opening extending completely through the slide holder, the inside surface having a flange extending into the opening, the slide holder being configured to receive the slide in the opening so that the slide rests on the flange;
    a slide cover at least partially disposed within the opening of the slide holder, the slide cover having a perimeter sidewall with a top surface and an opposing bottom surface, an inside surface extending between the top and bottom surfaces of the sidewall, the inside surface bounding an opening extending completely through the slide cover between the top and bottom surfaces of the slide cover, the slide cover being removably securable to the slide holder when positioned within the opening of the slide holder;
    a pair of electrodes positioned within the opening of the slide cover on opposite ends thereof; and
    a removable seal configured to be positioned between the slide cover and the slide so as to be aligned between the flange and the perimeter sidewall of the slide cover, such that when the slide is positioned within the opening of the slide holder so as to rest on the flange and the slide cover is secured to the slide holder with the seal positioned between the slide and the slide cover so as to be aligned with the flange, the slide is secured within the slide holder assembly and the inside surface of the slide cover and the top surface of the slide combine to form a cavity having an open top end, the cavity being water-tight and configured to hold a liquid therein.

2. The slide holder assembly as recited in claim 1, wherein each electrode comprises a bare wire extending across the opening.

3. The slide holder assembly as recited in claim 1, wherein the electrodes are parallel to one another.

4. The slide holder assembly as recited in claim 1, further comprising a pair of electrical connectors, each electrical connector being electrically coupled with a separate one of the electrodes, the electrical connectors being configured to electrically couple with an external power source.

5. The slide holder assembly as recited in claim 1, wherein the electrodes extend all the way across opposite sides of the slide cover.

6. The slide holder assembly as recited in claim 1, wherein the electrodes are disposed at or less than about 4 mm above the top surface of the slide when the slide is secured within the slide holder.

7. The slide holder assembly as recited in claim 1, wherein the electrodes are disposed at or less than about 2 mm above the top surface of the slide when the slide is secured within the slide holder.

8. The slide holder assembly as recited in claim 1, further comprising positioning aids extending from the inside surface of the slide cover, the positioning aids biasing against the electrodes.

9. The slide holder assembly as recited in claim 1, further comprising a lid removably positionable on the slide cover or the slide holder.

10. The slide holder assembly as recited in claim 1, wherein the slide holder assembly is configured to receive a 96-well slide.

11. A slide holder assembly for use in high-content screening, the slide holder assembly configured to receive a slide holding a plurality of biological cells, the slide having a top surface and an opposing bottom surface, the slide holder assembly comprising:
 a slide holder having a first perimeter sidewall comprising:
  a first top surface;
  an opposing first bottom surface; and
  a first inside surface extending between the first top and first bottom surfaces so as to bound a first opening extending completely through the slide holder, the first inside surface having a flange extending into the first opening, the slide holder being configured to receive the slide in the first opening so that the slide rests on the flange;
 a slide cover removably positionable within the first opening and removably securable to the slide holder when positioned within the first opening, the slide cover having a second perimeter sidewall comprising:
  a second top surface;
  an opposing second bottom surface; and
  a second inside surface extending between the second top and second bottom surfaces so as to bound a second opening extending completely through the slide cover, the second opening being aligned with the first opening when the slide cover is secured to the slide holder within the first opening;
 a pair of electrodes positioned within the second opening of the slide cover on opposite ends thereof; and
 a removable seal configured to be positioned between the slide cover and the slide so as to be aligned between the flange and the second perimeter sidewall, such that when the slide is positioned within the first opening so as to rest on the flange and the slide cover is positioned within the first opening and secured to the slide holder with the seal positioned between the slide and the slide cover so as to be aligned with the flange, the slide is secured within the slide holder assembly and the second inside surface and the top surface of the slide combine to form a cavity having an open top end, the cavity being watertight and configured to hold a liquid therein.

12. The slide holder assembly as recited in claim 11, wherein the slide holder assembly is configured to receive a 96-well slide.

13. The slide holder assembly as recited in claim 11, wherein each electrode comprises a bare wire extending across the second opening.

14. The slide holder assembly as recited in claim 11, wherein the electrodes are parallel to one another.

15. The slide holder assembly as recited in claim 11, further comprising a pair of electrical connectors, each electrical connector being electrically coupled with a separate one of the electrodes, the electrical connectors being configured to electrically couple with an external power source.

16. The slide holder assembly as recited in claim 11, wherein the electrodes extend all the way across opposite sides of the slide cover.

17. The slide holder assembly as recited in claim 11, wherein the electrodes are disposed at or less than about 4 mm above the top surface of the slide when the slide is secured within the slide holder assembly.

18. The slide holder assembly as recited in claim 11, wherein the electrodes are disposed at or less than about 2 mm above the top surface of the slide when the slide is secured within the slide holder assembly.

19. The slide holder assembly as recited in claim 11, further comprising positioning aids extending from the second inside surface of the slide cover, the positioning aids biasing against the electrodes.

20. The slide holder assembly as recited in claim 11, further comprising a lid removably positionable on the slide cover or the slide holder.

21. A slide holder assembly for use in high content screening of a comet assay, the slide holder assembly having an inside surface, the slide holder assembly being configured to receive a 96-well slide holding a plurality of biological cells on a top surface thereof, wherein when the slide is secured within the slide holder assembly, the inside surface of the slide holder assembly and the top surface of the slide combine to form a cavity having an open top end, the cavity including all of the wells of the slide, the cavity being watertight and configured to hold a liquid therein, a pair of electrodes being positioned within the cavity on opposite ends thereof.

22. The slide holder assembly as recited in claim 21, further comprising a lid removably positionable over the cavity.

23. The slide holder assembly as recited in claim 21, wherein the electrodes are parallel to one another.

24. The slide holder assembly as recited claim 21, further comprising positioning aids extending from the inside surface, the positioning aids biasing against the electrodes.

* * * * *